(12) United States Patent
Castellanos-Nolasco et al.

(10) Patent No.: US 7,024,031 B1
(45) Date of Patent: Apr. 4, 2006

(54) SYSTEM AND METHOD FOR INSPECTION USING OFF-ANGLE LIGHTING

(75) Inventors: Ramiro Castellanos-Nolasco, Richardson, TX (US); Sanjeev Mathur, Irving, TX (US); John Mark Thornell, Plano, TX (US); Thomas Casey Carrington, Plano, TX (US); Hak Chuah Sim, Garland, TX (US); Clyde Maxwell Guest, Plano, TX (US); Charles Kenneth Harris, Dallas, TX (US)

(73) Assignee: August Technology Corp., Bloomington, MN (US)

( * ) Notice: Subject to any disclaimer, the term of this patent is extended or adjusted under 35 U.S.C. 154(b) by 696 days.

(21) Appl. No.: 10/035,592

(22) Filed: Oct. 23, 2001

(51) Int. Cl.
G06K 9/00 (2006.01)

(52) U.S. Cl. .............. 382/141; 382/149; 382/199; 348/126; 250/559.16

(58) Field of Classification Search ............ 382/141, 382/142, 145, 147, 149, 143, 150, 151, 108, 382/199, 168, 173, 270, 294; 348/87, 126, 348/127, 92, 109; 358/464; 250/559.05, 250/559.16, 559.22, 559.11, 553
See application file for complete search history.

(56) References Cited

U.S. PATENT DOCUMENTS

| | | | |
|---|---|---|---|
| 5,058,178 A | 10/1991 | Ray | 382/8 |
| 5,164,994 A * | 11/1992 | Bushroe | 382/150 |
| 5,371,690 A * | 12/1994 | Engel et al. | 382/151 |
| 5,410,345 A * | 4/1995 | Eichenlaub | 348/59 |
| 5,455,870 A * | 10/1995 | Sepai et al. | 382/147 |
| 5,761,337 A * | 6/1998 | Nishimura et al. | 382/150 |
| 5,926,557 A | 7/1999 | King et al. | 382/149 |
| 6,181,425 B1 * | 1/2001 | Svetkoff et al. | 356/603 |
| 6,259,827 B1 * | 7/2001 | Nichani | 382/291 |
| 6,263,292 B1 | 7/2001 | Fiekowsky | 702/95 |
| 6,697,517 B1 * | 2/2004 | Hunter | 382/149 |
| 6,748,104 B1 * | 6/2004 | Bachelder et al. | 382/151 |

OTHER PUBLICATIONS

Search Report for PCT/US02/32531 Dated Dec. 27, 2002 in related PCT filing of pending U.S. Appl. No. 10/035,592.

* cited by examiner

*Primary Examiner*—Sheela Chawan
(74) *Attorney, Agent, or Firm*—Dicke, Billig & Czaja, PLLC (57) ABSTRACT

A system for inspecting components is provided. The system includes an axial lighting system that illuminates the component with axial lighting to allow one or more features of the component to be located, such as by causing protruding features to be brighter than the background and recessed features to be darker than the background. An off-axis lighting system illuminates the component with off-axis lighting in the absence of the axial lighting to allow the component to be inspected to locate one or more features, such as a bump contact.

25 Claims, 7 Drawing Sheets

SYSTEM AND METHOD FOR INSPECTION USING OFF-ANGLE LIGHTING

FIELD OF THE INVENTION

The present invention pertains to the field of component inspection systems. More specifically, the invention relates to a system and method for component inspection that uses off-angle lighting to illuminate features of the component that are of greatest interest.

BACKGROUND OF THE INVENTION

Inspections systems that use image data are known in the art. Such inspection systems typically use image data from a component that has been illuminated by either a coherent or noncoherent source, and then perform image analysis processes on the image data to determine whether the component conforms to predetermined criteria. For example, image data analysis is used to determine whether components have been properly marked, have features in the correct location, or have other specified criteria. In this regard, a "feature" can include a desired feature, such as a contact, or an undesired feature, such as damage on the contact that extends from or into the surface of the contact.

One problem with such component inspection systems is that three-dimensional aspects of the component must be inferred from the image data. Thus, in many cases it is difficult to determine whether an indication in the image data is from a feature that extends above or below a plane of reference. Likewise, since such image data analysis uses relative changes in brightness to infer the location of features and to determine whether such features fall within predetermined allowable criteria, it often occurs that the features are not distinguishable under a single lighting source. While it is known to use multiple lighting sources, such as lighting sources from two different angles, such lighting sources may still result in image data that does not clearly identify features of the component that do not meet specified criteria, such as to allow the size of features to be accurately determined.

SUMMARY OF THE INVENTION

In accordance with the present invention, a system and method for component inspection are presented that overcome known problems with component inspection.

In particular, a system and method for component inspection are provided that illuminate areas of interest lying above and below a planar surface of a feature by using off-axis lighting.

In accordance with an exemplary embodiment of the present invention, a system for inspecting components is provided. The system includes an axial lighting system that illuminates the component with axial lighting to allow one or more features of the component to be located, such as by causing particles or scratches to be darker than the background. An off-axis lighting system illuminates the component with off-axis lighting in the absence of the axial lighting to allow the component to be inspected to locate one or more features, such as by causing protruding features and damage to bump contacts to be brighter than the background.

The present invention provides many important technical advantages. One important technical advantage of the present invention is a system and method for inspecting components that uses off-angle lighting to identify damaged areas in a manner that allows image data analysis to be performed to identify protrusions and recesses in surfaces.

The present invention provides for accurate estimates of the size of such protrusions and recesses to be made from a single set of image data.

Those skilled in the art will further appreciate the advantages and superior features of the invention together with other important aspects thereof on reading the detailed description that follows in conjunction with the drawings.

DETAILED DESCRIPTION OF THE INVENTION

In the description that follows, like parts are marked throughout the specification and drawings with the same reference numerals, respectively. The drawing figures are not necessarily to scale, and certain components can be shown in generalized or schematic form and identified by commercial designations in the interest of clarity and conciseness.

Figure 1:
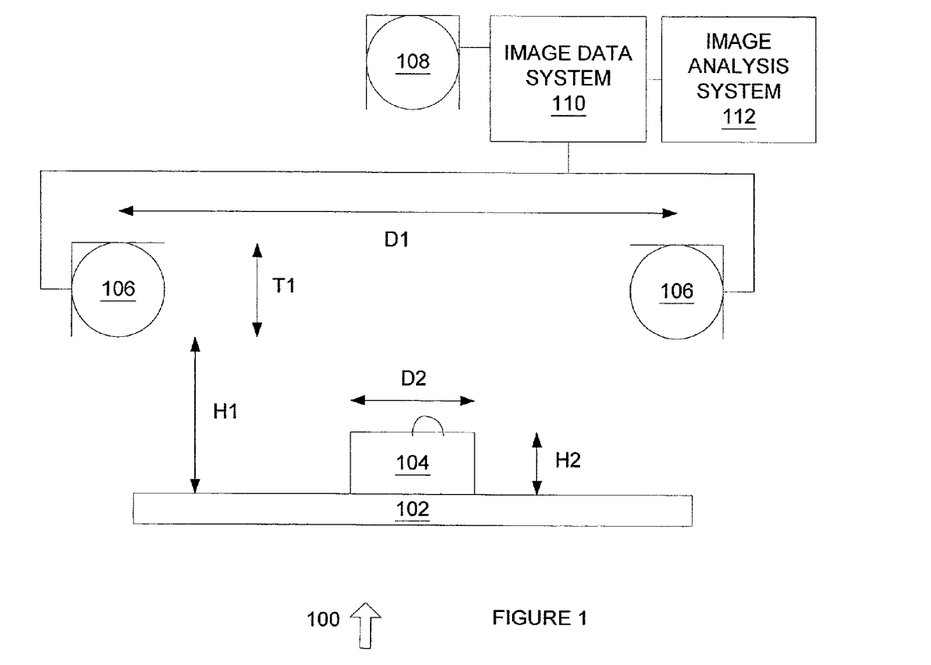
FIG. 1 is a diagram of a system for performing component inspection in accordance with an exemplary embodiment of the present invention.

FIG. 1 is a diagram of a system 100 for performing component inspection in accordance with an exemplary embodiment of the present invention. System 100 utilizes distributed off-axis lighting to create image data that clearly identifies components, features, and damage to such features that extends above or below a reference plane.

System 100 includes substrate 102, which can be a semiconductor die or other suitable materials on which one or more features have been placed, machined, deposited, or otherwise formed. Substrate 102 includes feature 104. In one exemplary embodiment, feature 104 can be a gold bump that is used to form a high quality electrical contact. In this exemplary embodiment, the size of feature 104 is significantly smaller than the size of other similar bumped contacts that are not formed from gold. For example, dimension D2 showing the length of feature 104 can be on the order of 50 to 90 micrometers, and H2, representing the height of the bump, can be on the order of 20 micrometers. Such dimensions are significantly smaller than solder bumps that are typically used to form electrical contacts with semiconductor circuits.

System 100 further includes off-axis lighting source 106, which can be a suitable off-axis lighting source that provides illumination of the entire surface of feature 104 and substrate 102 that is being inspected. In one exemplary embodiment, off-axis lighting source 106 can be a circular xenon flash lamp having a diameter D1 of approximately 1.5 inches, a thickness T1 of approximately 5 mm, and a height above substrate 102 H1 of approximately 2 mm. Xenon lighting may be required when zoom optics are used to increase the depth of field, as compared to microscope optics which do not require as much light intensity but provide less depth of field. Thus, where microscope optics provide sufficient depth of field, then an incandescent light source or other suitable light source can be used. (It should be noted that the dimensions in FIG. 1 are not shown to scale.)

Off-axis lighting source 106 illuminates feature 104 and substrate 102 in a manner that causes protrusions or recesses to be illuminated differently, such that protrusions and recesses can be distinguished from each other, and can be accurately analyzed to determine the size of the protrusion or recess. For example, one advantage of off-axis lighting source 106 is that the protrusion shown on feature 104 will appear brighter than the planar surface of feature 104 or the planar surface of substrate 102. Likewise, if feature 104 included a recess, then the recess would appear darker than the planar service of feature 104 or substrate 102. However, it may be difficult to distinguish between the planar surface of feature 104 and the planar surface of substrate 102 using off-axis lighting source 106. Whether or not it will be difficult to distinguish between the planar surface of feature 104 and the planar surface of substrate 102 will depend largely on the specific dimensions of feature 104, the materials from which feature 104 and substrate 102 are made from, and other factors. However, in some cases, while illumination with off-axis lighting source 106 can identify protrusions and recesses in planar surfaces, it may not be sufficient to provide useful distinction between planar surfaces of feature 104 and substrate 102.

Axial lighting source 108 provides conventional axial lighting of feature 104 and substrate 102. This axial lighting allows the surface of feature 104 and substrate 102 to be distinguished more readily, but may not provide sufficient indication of the existence of a protrusion or recess in the planar surface of feature 104. Thus, axial lighting source 108 can be used to locate the position of feature 104 on substrate 102, but might not be as useful in determining the existence of protrusions or recesses in the surface of feature 104.

Image data system 110 can be implemented in hardware, software, or a suitable combination of hardware and software, and can be one or more software systems operating on a general purpose processing platform. As used herein, a software system can include one or more objects, agents, lines of code, threads, subroutines, databases, application programming interfaces (APIs), web browser plug-ins, or other suitable data structures, source code (human readable), object code (machine readable), and can include two or more different lines of code or suitable data structures operating in two or more separate software applications, on two or more different processing platforms, or in other suitable architectures. In one exemplary embodiment, a software system can include one or more lines of code or other suitable software structures operating in a general purpose software application, such as an operating system, and one or more lines of code or other suitable software structures operating in a specific purpose software application. In another exemplary embodiment, a software system can be implemented as a distributed software system, on a different processing platform than that shown in the exemplary embodiments herein, or in other suitable manners.

Image data system 110 is coupled to axial lighting source 108 and off-axis lighting source 106. As used herein, the term "couple," and its cognate terms such as "couples" and "coupled," can include a physical connection (such as through a copper conductor), a virtual connection (such as through randomly assigned memory locations of a data memory device), a logical connection (such as through one or more logical devices of a semiconducting circuit), other suitable connections, or a suitable combination of such connections. In one exemplary embodiment, systems and components are coupled to other systems and components through intervening systems and components, such as through an operating system of a general purpose server platform.

Image data system 110 generates image data of feature 104 and substrate 102. In one exemplary embodiment, image data system 110 can control axial lighting source 108 and off-axis lighting source 106 so that first image data is generated using axial lighting source 108, such as to locate features 104 on substrate 102. Then, second image data is generated using only off-axis lighting source 106, such as to analyze the surface of feature 104 to determine whether protrusions or recesses are present. Image data system 110 generates image data, such as an N×M array of pixels (where N and M are integers) having brightness values ranging from 0 (representing the darkest or least bright pixel value) to 255 (representing the brightest or most bright pixel value), or other suitable ranges of brightness values.

Image analysis system 112 can be implemented in hardware, software, or a suitable combination of hardware and software, and can be one or more software systems operating on a general purpose processor platform. Image analysis system 112 is coupled to image data system 110, and obtains the image data generated by image data system 110, both for direct and off-axis illumination. Image analysis system 112 then analyzes the image data to identify the location of feature 104 and other similar features, and to further analyze feature 104 and other features to determine whether protrusions or recesses exist in the surface of such features that renders them unusable. In one exemplary embodiment, image analysis system 112 can use pixel image processing to identify the location of feature 104 and other features, and whether such features are damaged. This pixel image processing can include determining whether adjacent pixels have a gradient that exceeds known allowable gradient differentials, whether a histogram of pixels of the image data indicate the existence of damage, such as protrusions or recesses, or other suitable processes. Image analysis system 112 analyzes image data from off-axis lighting source 106, so as to provide identification of damage that may otherwise be difficult to identify.

In operation, system 100 is used to inspect components to determine whether the components meet predetermined allowable criteria. In one exemplary embodiment, system 100 can be used to inspect gold bumps or other small features that have heretofore been difficult or impossible to inspect using image data analysis. System 100 allows the entire surface of a component to be illuminated in a manner that allows bulk processing of the image data of the component to be performed, such as histogram processing, gradient processing, or other suitable bulk imaging techniques. In this manner, system 100 reduces the need for performing laser tracking or point analysis of images, such as where the laser must be traced or placed at predetermined points that cover all features of interest of the component.

System 100 further improves on inspection techniques by providing two lighting sources for two different component inspection functions. System 100 uses a first lighting source to align the component for inspection, and a second lighting source to inspect the component to identify damage to the component. In this manner, system 100 uses two or more lightning sources in a manner where each lighting source performs a different function.

Figure 2:
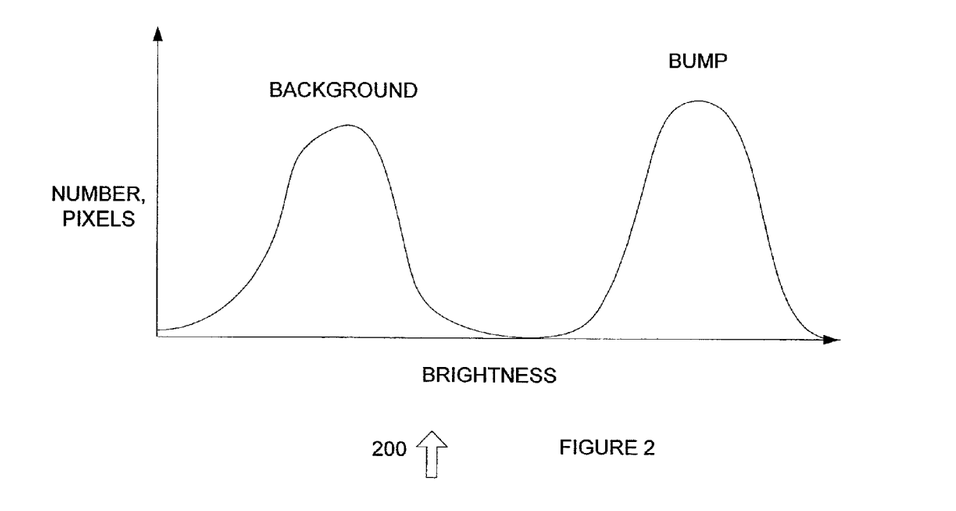
FIG. 2 is an exemplary histogram of pixel brightness data in accordance with an exemplary embodiment of the present invention.

FIG. 2 is an exemplary histogram 200 of pixel brightness data in accordance with an exemplary embodiment of the present invention. Histogram 200 shows a plot of brightness magnitude versus the number of pixels having that brightness magnitude for an exemplary image. Brightness value increases with increasing x-axis values, and number of pixels increases with the increasing y-axis values. In this exemplary embodiment, histogram 200 includes two maxima. The first maximum, having the lower brightness values, is representative of the background pixel brightness values. The second maximum, having the higher brightness values, is representative of the feature pixel brightness data. The brightness data of histogram 200 can be generated from off-axis lighting source 106, or axial lighting, such as from axial lighting source 108 (in which case the histogram is reversed, such that the first maximum represents the bump and the second maximum represents the background. Thus, histogram 200 can be used to locate the position of features, by using the coordinate data from the pixels of the second maximum. In this manner, an initial location of features can be performed.

Likewise, a gradient selection method can also be used to identify features and the edge of such features. For example, the CVLMIL software available from Semiconductor Technologies and Instruments of Plano, Tex. includes a gradient analysis tool that analyzes image data to locate edges, such as by detecting gradient changes in pixels of image data. In this exemplary embodiment, if the area within a feature is brighter than the surrounding area, then the edge can be located by analyzing a predetermined R×S block of pixels (where R and S are integers) along either the R or S axis until a gradient is detected between pixel values within the R×S block that is greater than a predetermined allowable gradient. If the pixels outside of the feature are dark and the pixels within the feature are light, then as the R×S block of pixels moves onto the feature, the gradient of the pixels within the block will go from a predetermined allowable gradient to a gradient that exceeds the predetermined allowable amount and back to the predetermined allowable gradient. Thus, the approximate location of the edge can be inferred from the weighted midpoint of the transition between the flat gradient in the dark area and the flat gradient in the light area. Other suitable procedures can be used to locate the edge of a bump or feature.

Figure 3:
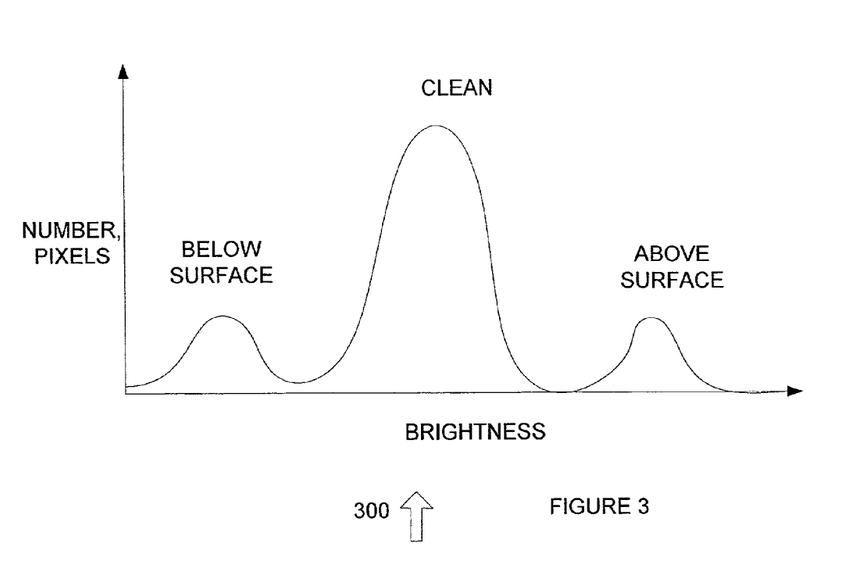
FIG. 3 is a histogram showing pixel analysis data in accordance with an exemplary embodiment of the present invention.

FIG. 3 is a histogram 300 showing pixel analysis data in accordance with an exemplary embodiment of the present invention. Histogram 300 shows 3 relative maxima in the histogram data. The first relative maximum, having a peak at the highest brightness value, is indicative of protrusions or other above surface damaged areas when they are illuminated with a light source such as off-axis lighting source 106. In this exemplary embodiment, the off-axis light source causes such protrusions to be brighter than the feature from which they protrude, such as feature 104. Histogram 300 further includes a second relative maximum, which is indicative of all the clean portions of the planar surface. The third maximum at the darkest end of the brightness axis is indicative of damage that extends below the surface or is recessed, such as scratches, indentations, probe marks or other similar damage. When illuminated by a light source such as off-axis lighting source 106, then such recesses into the surface will generate lower than average pixel brightness.

Histogram 300 is used to locate areas requiring additional inspection by associating the pixels in the above surface and below surface relative maxima with their locations in the N×M array of pixel data. These pixels can then be further analyzed to determine whether they are indicative of damage, scratches, dust spots, or for other suitable purposes.

Figure 4:
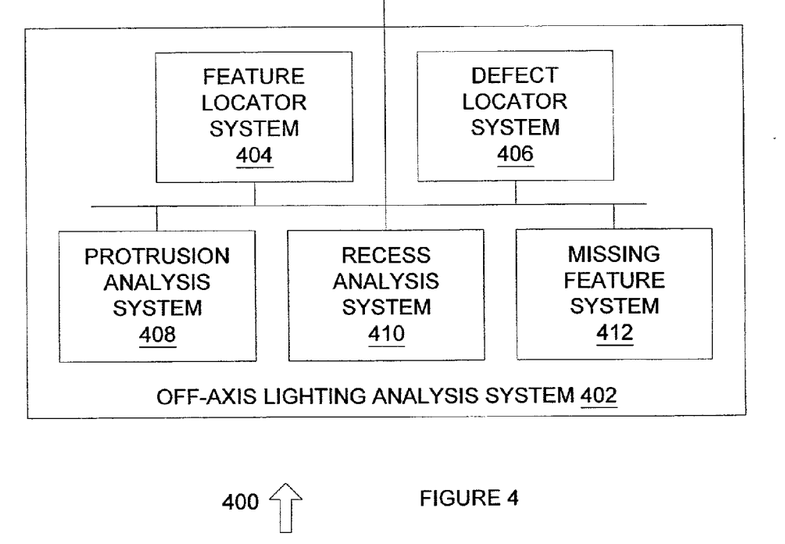
FIG. 4 is a diagram of system for performing off-axis lighting analysis in accordance with an exemplary embodiment of the present invention.

FIG. 4 is a diagram of system 400 for performing off-axis lighting analysis in accordance with an exemplary embodiment of the present invention. System 400 includes feature locator system 404, defect locator system 406, protrusion analysis system 408, recess analysis system 410, and missing feature system 412, each of which can be implemented in hardware, software, or a suitable combination of hardware and software, and which can be one more software systems operating on a general purpose processing platform.

Feature locator system 404 identifies the location of one or more features of a component, such as gold bump contacts. In one exemplary embodiment, feature locator system 404 identifies features when axial lighting is used, and then generates a suitable edge boundary indicator for use in analyzing the image data when off-axis lighting is used. Likewise, feature locator system 404 can also be used to locate the edges of features using only off-axis lighting when the design and material composition of the component allow such functionality. Feature locator system 404 can also perform histogram analysis of data to identify the location of one or more features, such as by plotting the histogram of pixel brightness values as a function of the number of pixels to locate features, and then performing additional image analysis to verify that the feature indication is actually a feature, such as by using gradient analysis to identify the edges of the feature.

Defect locator system 406 is used to identify one or more defects in image data generated by off-axis lighting. In one exemplary embodiment, defect locator system 406 receives image data after analysis by feature locator system 404, and performs additional histogram data analysis on one or more features that have been identified. In this exemplary embodiment, features of a component such as gold bumps can be first identified using histogram data, and then a second set of histogram data can be generated for individual features, so as to identify damage to those features, where each damage location itself is a "feature" for the purpose of image data analysis. Defect locator system 406 can include predetermined tolerances for histogram data that have been empirically matched with protrusion damage, such as nodules, recess damage such as scratches or mouse bites, or other damage.

Protrusion analysis system 408 receives image data and generates protrusion data. In one exemplary embodiment, the image data can include predetermined areas that have a brightness value that exceeds the expected brightness value of the surface of the feature, such that protrusion analysis system 408 can then analyze the feature to determine whether it is of a size that exceeds predetermined allowable protrusions. In this exemplary embodiment, a morphologic opening algorithm can be used to remove a predetermined number of perimeters from a suspected protrusion feature, such that if all of the pixels defining the protrusion have been removed prior to completion of the morphological opening algorithm, then the size of the corresponding anomaly can be determined to be below a specified allowable tolerance. Other suitable processes can be used.

Recess analysis system 410 is used to analyze image data generated by off-axis lighting to identify one or more recess features, such as scratches, mouse bites, probe marks or other such recess damage. In one exemplary embodiment, recess analysis system 410 identifies areas where the pixel brightness is lower than a predetermined tolerance, such as by using a histogram analysis. These areas are then analyzed to further determine the size and gradient of the area, so as to determine whether it is representative of damage. For example, the gradient can be determined by analyzing the change in brightness over the length of the suspected damaged area, such as to be compared to empirically determined allowable damage (e.g. allowable lengths of scratches, allowable width of scratches), or other suitable data. Likewise, the total approximated area encompassed by a scratch or other recess feature can be determined. Recess analysis system 410 can then compare the recess analysis data to predetermined allowable sizes, and can generate recess data indicating the existence of a recess that is unacceptable.

In one exemplary embodiment, a scratch or other recess on a feature can be identified by performing a row and column projection, such as by summing all pixels in a row of each column of an S×T array of pixels (where S and T are integers), and taking the average of those pixel values. Likewise, a similar procedure can be used for all pixels in a column of each row of the S×T array. For example, in the 4×6 array of pixel values represented as follows:

| 100 | 100 | 100 | 100 | 100 | 100 |
| 100 | 80  | 60  | 80  | 100 | 100 |
| 100 | 20  | 0   | 20  | 60  | 100 |
| 100 | 100 | 100 | 100 | 100 | 100 |

The row and column projections described above would yield:
100 65 75 90 100 and
100
86.7
50
100

It may be empirically determined that row or column projections resulting in gradients that exceed a predetermined number of adjacent pixels (such as four or more) or that have a predetermined maximum or percentage change in value (such as more than 50 relative brightness points on a 256 point scale) can result in unacceptable levels of misoperation, such that the features on which such damage is present should be rejected. Thus, in this exemplary embodiment, the damage to the feature would be held to be unacceptable based on the failure of either of two criteria. Likewise, if both criteria included boundaries of allowable values for row and column projections (such as reject for 6 or more pixels, borderline 5 to 4 pixels, and accept 3 or less pixels), then the feature could be classified as unacceptable based upon the fact that both criteria are borderline, based on the area of the damage, or based on other or additional damage indicators. The values given here are by way of example only, and other suitable types of processes can be used also or alternatively to those described herein.

Missing feature system 412 can receive image data and determine whether one or more features are missing from the image data. In one exemplary embodiment, after a feature template has been generated either by operator selection or image analysis with feature locator system 404, a template can be generated that outlines the expected location of one or more features. Missing feature system 412 can analyze image data, such as pixels of brightness data, of the expected feature locations, and can generate missing feature data if the number of pixels having a certain brightness value or greater in an area where a feature is expected is significantly less than the expected number. In this manner, missing feature system 412 can generate missing feature data that indicates an unacceptable device or other suitable data.

In operation, system 400 receives image data generated with off-axis lighting and analyzes the image data to determine whether a protrusion, recess or other similar damage exists in the image data. System 400 thus allows image data features to be analyzed to determine whether the features meet predetermined criteria.

Figure 5:
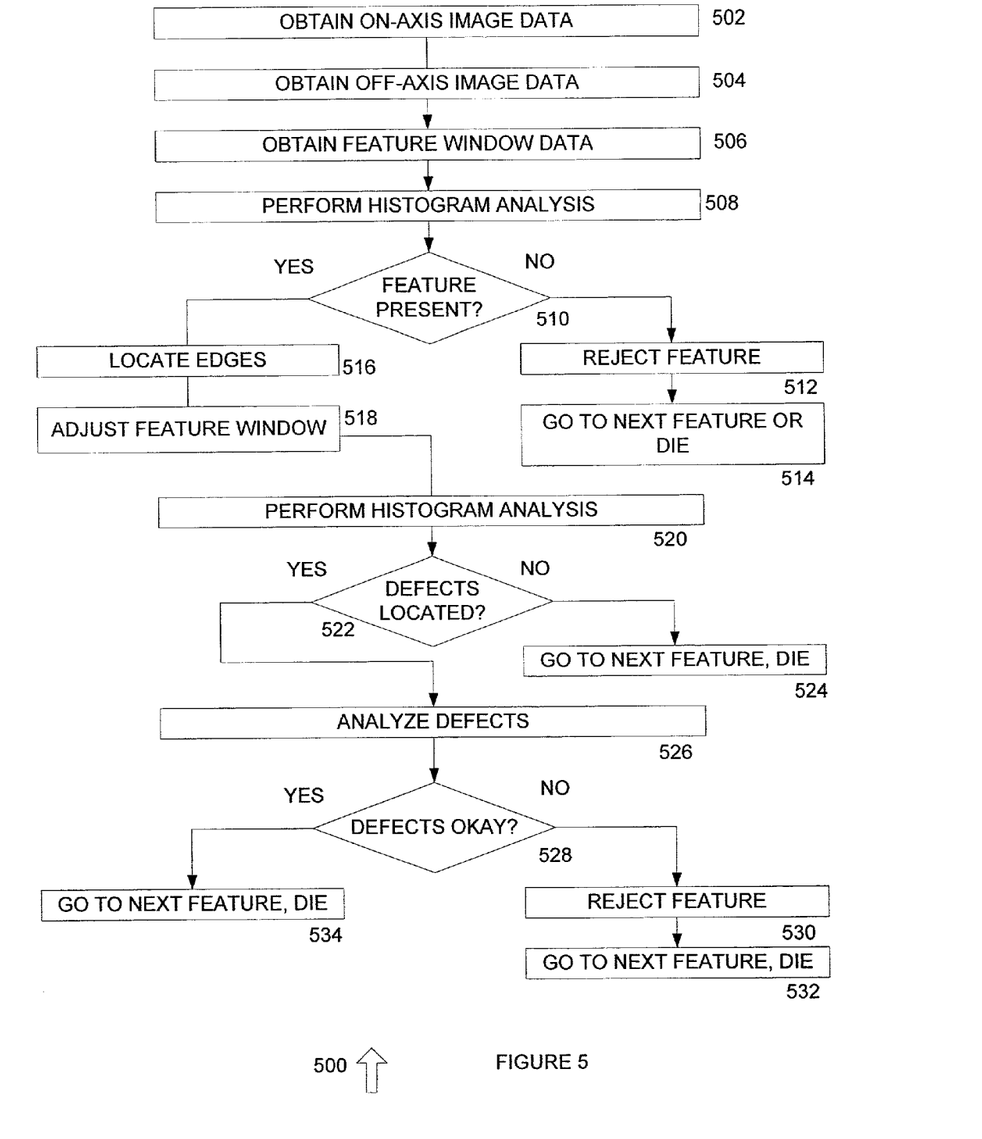
FIG. 5 is a flowchart of a method for inspecting a component using off-axis lighting in accordance with an exemplary embodiment of the present invention.

FIG. 5 is a flowchart of a method 500 for inspecting a component using off-axis lighting in accordance with an exemplary embodiment of the present invention. Method 500 begins at 502 where axial image data is obtained. The axial image data can include image data obtained from axial lighting of a component or other suitable axial image data. The method then proceeds to 504.

AT 504, feature window data is generated. In one exemplary embodiment, the feature window data can include a perimeter line generated based on user selected criteria, pixel gradient data, or other suitable data that is used to identify the outline of a feature and to generate a window. The window can also be enlarged by a predetermined amount. The method then proceeds to 506.

At 506, off-axis image data is generated. The off-axis image data is generated by illuminating the component with off-axis lighting, and generating image data when the component is so illuminated. For example, the component can be illuminated using a circular xenon flash lamp that is placed parallel and adjacent to the surface of the component. Likewise, other suitable processes can be used to generate the off-axis image data by using lighting that uniformly illuminates the surface of the feature so as to cause recessed areas to be darker than planar surfaces and to cause protrusions to be brighter than planar surfaces. The method then proceeds to 508.

At 508, the edges of the feature are located. In one exemplary embodiment, the edges can be located using a gradient method or process, such as by using the Matrox Imaging Library "Blob Analysis" tool or other suitable image analysis procedures. The method then proceeds to 510.

At 510, it is determined whether the feature is acceptable. For example, if it is determined that the feature is not acceptable, such as if the feature has unacceptable dimensions, the feature is missing, or other unacceptable conditions exist, the method proceeds to 512 where the feature is rejected. An error message can be also or alternatively be generated, log data can be generated indicating that the feature is unacceptable, or other suitable rejection procedures can be used. The method then proceeds to 514. At 514, the next feature or die is analyzed, such as by initiating method 500 again.

If it is determined at 510 that the edges of the feature are acceptable, the method proceeds to 516, where a histogram analysis is performed. In one exemplary embodiment, the histogram analysis can be performed for each feature, can be performed on all features of the component, or other suitable histogram analyses can be performed. The method then proceeds to 518.

At 518 it is determined whether defects or "damage features" have been located within the boundary that defines the feature. In one exemplary embodiment, one or more tolerance levels can be set, either through analysis, empirically or otherwise, that identify acceptable levels for histogram brightness distribution data. If the pixel brightness data of the histogram exceeds these predetermined levels, it can be determined that a defect is present or may be present. If a defect indication has not been located, the method proceeds to 520 and the next feature or die is analyzed, such as by beginning method 500 over from the beginning. Otherwise, the method proceeds to 522.

At 522, the defect indication is analyzed. For example, the defect can include an area where the pixels are brighter than allowable, indicating a protrusion or other similar above surface defect, an area where the pixels are darker than expected, indicating a recess or area where other subsurface damage has occurred, or other similar defects. The defects can be analyzed to determine the size, the area, the brightness gradients, or other suitable dimensions of the defects. The method then proceeds to 524.

At 524 it is determined whether the defects are acceptable. In one exemplary embodiment, the results from the defect indication analysis are compared to acceptable boundaries or limits for such dimensions. If it is determined that the defects are acceptable, the method proceeds to 526 and the next feature or die is analyzed, such as by initiating method 500 for that feature or die. Otherwise, the method proceeds to 528 and the feature is rejected, such as by generating feature rejection data, marking the feature as rejected, or performing other suitable processes. The method then proceeds to 530 and the next feature or die is analyzed.

In operation, method 500 is used to analyze feature data generated from off-axis lighting. Method 500 allows protrusions and recesses in feature surfaces to be identified by analysis of off-axis lighting data. Likewise, method 500 allows axial lighting to be used to identify the feature, generate feature edge windows, or for other suitable purposes.

Figure 6:
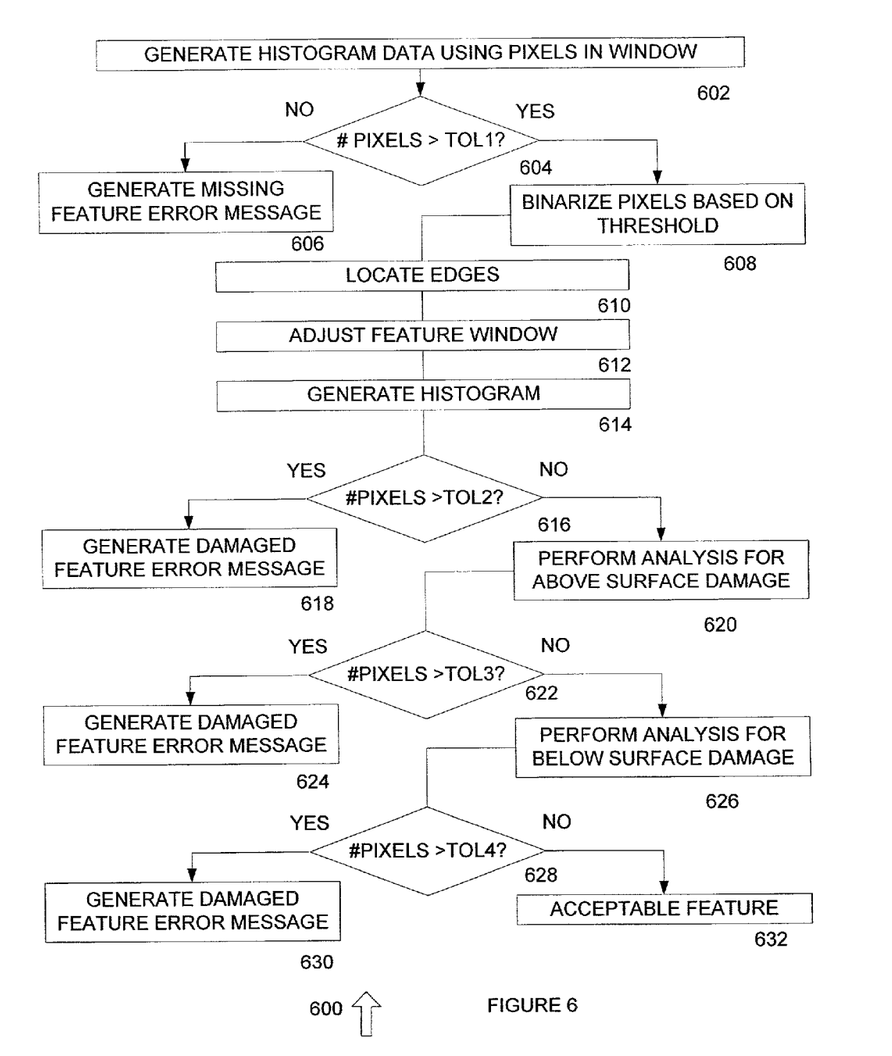
FIG. 6 is a flowchart of a method for analyzing off-axis image data in accordance with an exemplary embodiment of the present invention.

FIG. 6 is a flowchart of a method 600 for analyzing off-axis image data in accordance with an exemplary embodiment of the present invention. Method 600 allows off-axis image data of the component to be analyzed to locate protrusions, recesses or other damage features of the component.

Method 600 begins at 602 where histogram data is generated using pixels and a feature window. The feature window can be generated by circumscribing the feature with a boundary, such that all pixels within the boundary are analyzed. The method then proceeds to 604.

At 604 it is determined whether the number of pixels having a brightness that exceeds a first tolerance level exists. For example, the number of allowable pixels having a brightness that exceeds the first tolerance level can be empirically determined, the slope of the histogram data can be analyzed to determine whether a maximum occurs having a peak greater than a predetermined tolerance, or other suitable procedures can be used. If it is determined at 604 that the number of pixels is greater than the first tolerance level, the method proceeds to 606, where an analysis is performed for damage above the surface of the feature. For example, the pixels having brightness values that exceed the predetermined tolerance can be analyzed to determine whether they form an area having a size that is greater than a predetermined allowable tolerance. Other suitable procedures can be used. The method then proceeds to 608. Likewise, if it is determined at 604 that the number of pixels exceeding the tolerance level is not greater than a predetermined allowable number, the method proceeds directly to 608.

At 608 it is determined whether a predetermined number of pixels having a brightness value between the first tolerance level and a second tolerance level exists. If the number of pixels exceeding the second tolerance level but less than the first tolerance level is less than a predetermined number, the method proceeds to 610 where a missing feature error message is generated. In one exemplary embodiment, if the feature window is generated automatically, such as by using a reference feature to locate a feature window template on a component, it is possible that a missing feature would be included in the window, with the result that the window would contain a large number of pixels not having a brightness value that is expected. In this exemplary embodiment, the missing feature error message can be generated, the feature can be flagged as being missing, an operator notification can be generated or other suitable procedures can be implemented. The method then proceeds to 614. Likewise, if it is determined at 608 that the number of pixels having brightness values between the first and second tolerance levels exists, then the method proceeds to 612 where the feature is indicated to be acceptable, meaning that it is in the correct location and is not missing. The method then proceeds to 614.

At 614 it is determined whether a number of pixels is less than a third tolerance level, which can be equal to or less than the second tolerance level. If the number of pixels is less than this level, the method proceeds to 616 where an analysis is performed to identify below surface damage. In one exemplary embodiment, the coordinates of the pixels that fall below the third tolerance level can be identified and the size, gradient and other characteristics of the areas encompassed by such pixels can be analyzed to determine whether the characteristics indicate that damage exists. Otherwise, if it is determined at 614 that the number of pixels having brightness values less than the third tolerance level does not exceed predetermined levels, then the method proceeds to 618 and terminates.

In operation, method 600 allows off-axis lighting to be used to generate image data that is then analyzed to determine whether a feature has above surface damage, below surface damage, whether the feature is missing, or whether other damage conditions exist. Method 600 thus allows features to be analyzed to reliably and quickly locate damage that may otherwise be difficult to locate when using only axial lighting or other existing image analysis and inspection techniques.

Figure 7:
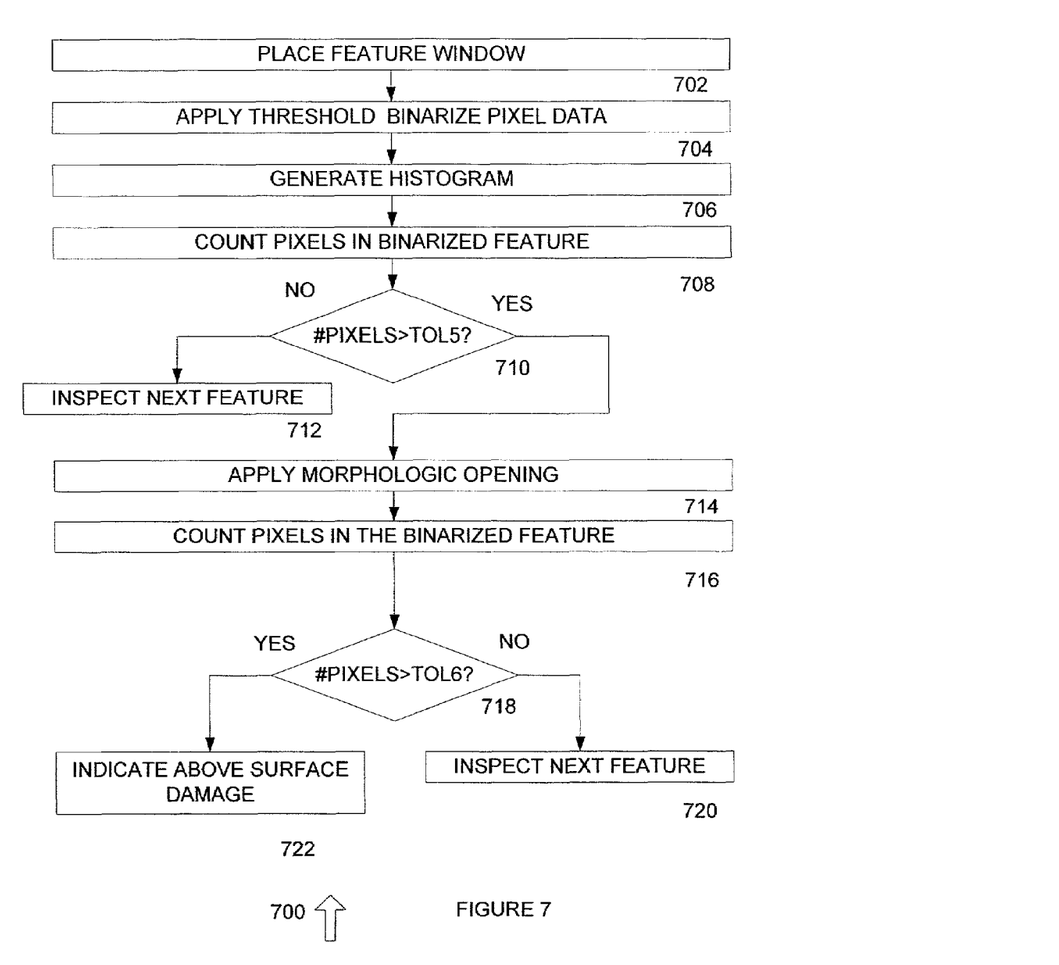
FIG. 7 is a flowchart of a method for determining whether a protrusion is present on the surface of a feature in accordance with an exemplary embodiment of the present invention.

FIG. 7 is a flowchart of a method 700 for determining whether a protrusion is present on the surface of a feature in accordance with an exemplary embodiment of the present invention. Method 700 begins at 702 where defects are located using pixels having a brightness value that is greater than a predetermined tolerance, such as from image data generated by off-axis lighting. The method then proceeds to 704 where a first pixel in a test area is selected. In one exemplary embodiment, the pixel can be selected by locating a pixel on the edge of an area, such as by using a gradient differential technique, by determining the mathematical edge using pixel coordinate data, or other suitable processes. The method then proceeds to 706.

At 706, the pixel in the test area is blacked out. For example, the pixel brightness data can be set to 0, a set of pixels in the test area can be identified and data corresponding to the selected pixel can be stored to indicate that the pixel has been checked, or other suitable procedures can be used. The method then proceeds to 708.

At 708 it is determined whether a predetermined integer or other suitable number of times of dilation around the test area have been performed. For example, if the test area is a circular region having a diameter of 10 pixels, then performing an erosion around the test area one time would result in an area having a pixel diameter of 8 pixels, performing a second dilation two times around would result in an area having a diameter of 6 pixels, and so forth. The number of times around the test area can be determined by tracking the progress of erosion relative to the first pixel, or by other suitable methods. If it is determined that the pixels have been blacked out N times around, the method proceeds to 716. Otherwise, the method proceeds to 710 where an adjacent pixel is selected in the test area. In one exemplary embodiment, each of the pixels adjacent to the pixel just blacked out can be checked to determine which pixel is brightest, which pixel is on an edge of the remaining test area pixels, whether any of the pixels have a brightness value that exceeds a predetermined brightness value, or other suitable procedures can be used. The method then proceeds to 712.

At 712 is determined whether an adjacent pixel was located. If an adjacent pixel is not located, the method proceeds to 714 and the indication is cleared as being damage having a greater than an allowable size. Otherwise, the method returns to 706.

After a predetermined number of erosions have been performed on the test area, the method proceeds to 716 where it is determined whether there are any pixels left. For example, if the dilations have resulted in the elimination of all pixels in the test area, the method proceeds to 720 where the indication of a potential anomaly is cleared. Otherwise the method proceeds to 718 where an indication is generated of the presence of a potential anomaly, nodule, or other protrusion type of damage.

In operation, method 700 performs a morphologic opening analysis to determine the size of a protrusion, such as by using pixel brightness generated from off-axis lighting. Method 700 thus allows a nodule or other similar protrusions to be identified. The number of times around at step 708 can be set to equal a customer specified allowable size for a nodule, can be set based on analytical or empirical data, or other suitable data.

Figure 8:
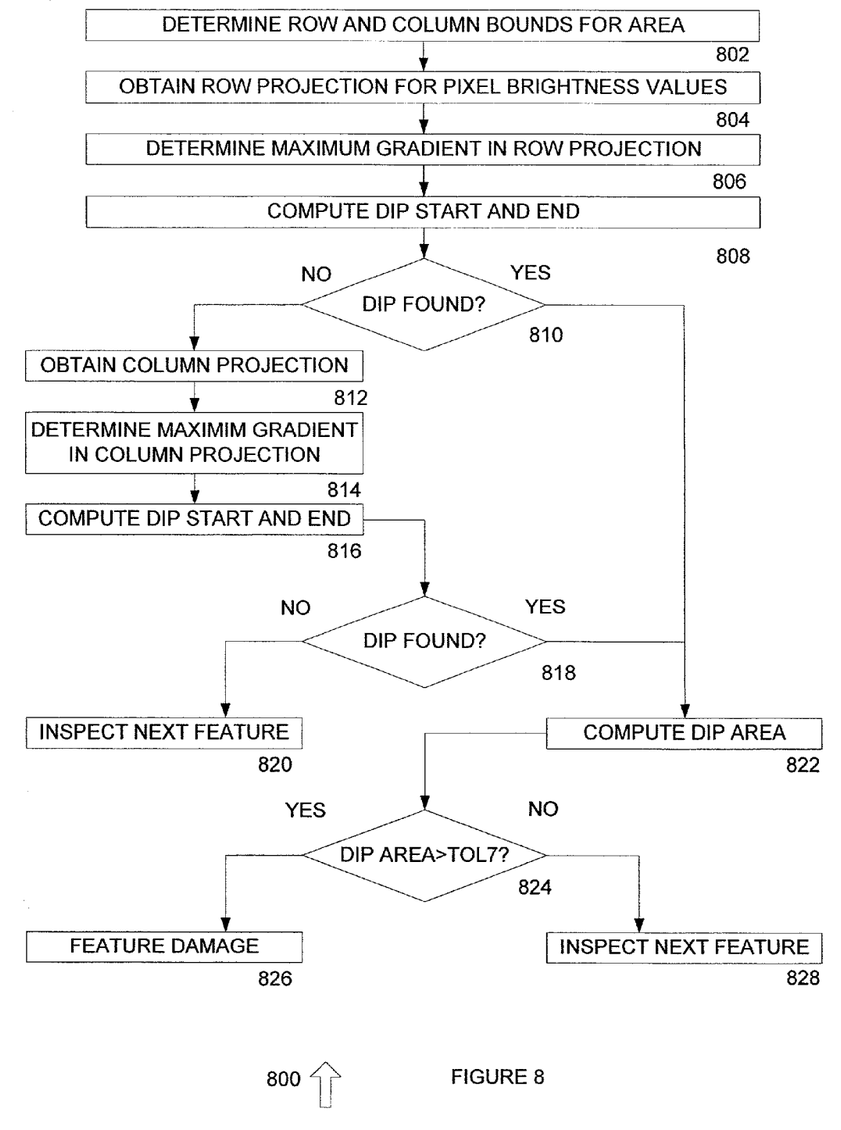
FIG. 8 is a flowchart of a method for analyzing subsurface damage in a feature in accordance with an exemplary embodiment of the present invention.

FIG. 8 is a flowchart of a method 800 for analyzing subsurface damage in a feature in accordance with an exemplary embodiment of the present invention. Method 800 begins at 802 where the row and column bounds for a suspect area are determined. In one exemplary embodiment, the suspect area can be determined by generating histogram data from off-axis lighting, and selecting pixels having a brightness less than a tolerance level. The coordinates of such pixels can then be used to identify the test area. The row and column bounds for the test area can be generated by selecting the row and column of pixels outside of the test area, such as by using a gradient method. The method then proceeds to 804.

At 804, a row projection of pixel brightness values is obtained. In one exemplary embodiment, the pixel brightness values for all pixels in the columns of each row entry can be averaged, such as to perform a row projection of the pixel brightness values. The method then proceeds to 806.

At 806, a column projection of pixel brightness values is obtained. In one exemplary embodiment, the pixel brightness values of each pixel in a row extending from a column can be averaged for that column, such as to create a column projection for pixel brightness values. The method then proceeds to 808.

At 808, it is determined whether the size of the recess damage area is greater than a predetermined tolerance value. In one exemplary embodiment, size can be estimated by using the number of pixels over which the row projection and column projection extend, to estimate a size of the recess damage. If the size is greater than the tolerance, the method proceeds to 810 and the indication is rejected as having a size greater than tolerance. Otherwise, the method proceeds to 812.

At 812 it is determined whether the row gradient exceeds an allowable tolerance. The allowable tolerance can be generated empirically or through analysis, in accordance with customer specifications, or in other suitable manners. For example, the allowable tolerance can include a maximum brightness differential between the brightest and the darkest pixels, a maximum allowable differential between any two adjacent pixels, or other suitable gradient tolerances. If the row gradient exceeds the tolerance, the method proceeds to 814 and the indication is rejected. Otherwise, the method then proceeds to 816.

At 816 it is determined whether the column gradient exceeds an allowable tolerance. The allowable tolerance can be generated empirically or through analysis, in accordance with customer specifications, or in other suitable manners. If it is determined at 816 that the column gradient exceeds the tolerance, the method proceeds to 818 and the indication is rejected. Otherwise, the method proceeds to 820.

At 820 it is determined whether the combination of size, row gradient, and column gradient is acceptable. In one exemplary embodiment, the customer can specify maximum values for each measurement, maximum values for the combination of values can be determined empirically, or other suitable processes can be used. Further, borderline values can be identified where the combination of values is analyzed when one or more values are borderline. If it is determined at 820 that the combination is acceptable, the method proceeds to 822 and the indication is rejected. Otherwise, the method proceeds to 824 and the indication is cleared.

In operation, method 800 allows subsurface damage to be analyzed to determine whether it is allowable. In one exemplary embodiment, method 800 uses off-axis lighting to generate pixel data which is analyzed to determine whether recesses, scratches, mouse bites, probe marks, or other damage has resulted in an unallowable feature.

Figure 9:
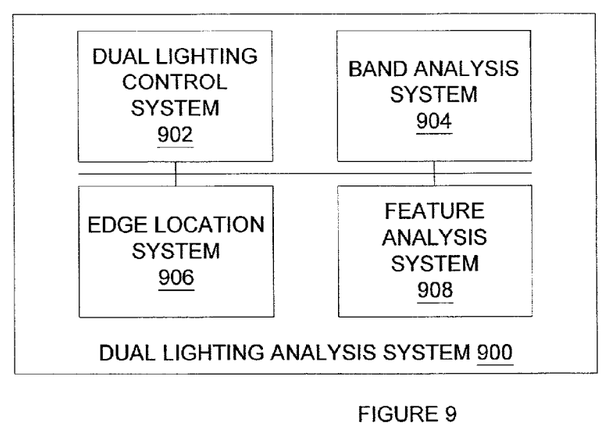
FIG. 9 is a diagram of a system for analyzing dual lighting image data in accordance with an exemplary embodiment of the present invention.

FIG. 9 is a diagram of a system 900 for analyzing dual lighting image data in accordance with an exemplary embodiment of the present invention. System 900 can be used to locate sunken ball contacts and other anomalies.

System 900 includes dual lighting control system 902, band analysis system 904, edge location system 906 and feature analysis system 908, each of which can be implemented in hardware, software, or a suitable combination of hardware and software, and which can be one or more software systems operating on a general purpose processing platform. Dual lighting control system 902 controls two or more light sources, such as an axial light source and an off-axis light source, so as to illuminate a component with the two or more light sources. In one exemplary embodiment, the off-axis light source can be a ring of light-emitting diodes or other suitable light sources. In another exemplary embodiment, dual lighting control system 902 can control two or more light sources in a predetermined sequence, such as to generate two or more different sets of image data when the component is illuminated with two or more different sets of light sources.

Band analysis system 904 receives edge data and determines whether a band is present in a set of image data. In one exemplary embodiment, band analysis system 904 can receive edge coordinate data that identifies two or more edges between dark areas and light areas in a set of image data, and can generate band data that identifies whether the edges define a circular band, such as a band created by a sunken ball contact when it is illuminated with an axial light source and an off-axis light source at the same time, or other suitable bands. Such bands can be indicative of an anomaly, such as a sunken ball contact, that may render the component inoperative. Band analysis system 904 can further receive edge data from two or more different locations and other feature data, such as component center data, and can determine whether a band exists based on the edge data and the other feature data.

Edge location system 906 analyzes image data and generates edge data. In one exemplary embodiment, edge location system 906 searches for edges by analyzing brightness data differences in adjacent pixels, where an edge is defined by a predetermined brightness data difference, a set of predetermined brightness data differences (such as in two or more sets of adjacent pixels), or other suitable data. In another exemplary embodiment, edge location system 906 can analyze pixel brightness data in predetermined locations, relative to predetermined component features, using histogram analysis, or using other suitable processes.

Feature analysis system 908 receives image data, band data, edge data, or other suitable data and determines whether a feature is present, such as a sunken ball contact. In one exemplary embodiment, feature analysis system 908 can determine whether a band width exceeds a predetermined allowable band width, whether a band extends for a predetermined length or periphery, or other band-related feature data, such as to indicate whether a sunken ball contact or other anomaly is present. Likewise, missing features, protrusions, scratches, or other damage can be detected by feature analysis system 908, and notification data can be generated to alert an operator, remove the component from production, or perform other suitable procedures. Feature analysis system 908 generates feature or component acceptance data, feature or component rejection data, operator data alerting the operator of the need for operator inspection, or other suitable data.

In operation, system 900 allows a component to be inspected using two or more light sources that illuminate the component simultaneously, such as an axial light source and an off-axis light source. System 900 can be used to locate sunken ball contacts or other anomalies by locating image data that indicates the presence of such anomalies, such as a circular ring that appears around a sunken ball contact when it is illuminated by an axial light source and an off-axis light source.

Figure 10:
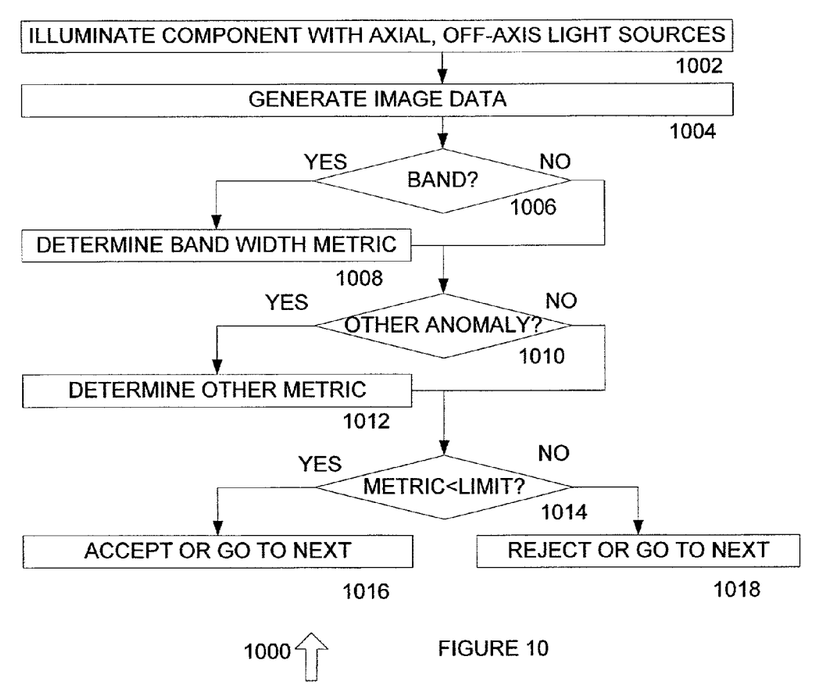
FIG. 10 is a flow chart of a method for analyzing dual lighting image data in accordance with an exemplary embodiment of the present invention.

FIG. 10 is a flow chart of a method 1000 for analyzing dual lighting image data in accordance with an exemplary embodiment of the present invention. Method 1000 begins at 1002, where a component is illuminated with an axial light source and an off-axis light source. In one exemplary embodiment, the off-axis light source can be a ring arrangement of light-emitting diodes, or other suitable circular light sources. The method then proceeds to 1004.

At 1004, image data of the component is generated, such as by generating an N×M array of pixels of brightness data. The method then proceeds to 1006, where it is determined whether a band is present. In one exemplary embodiment, the band can be detected by locating two or more edges in the N×M array of pixel data, such as edges at two or more points, a continuous edge that extends in a line or circle, or other suitable data. If no band is present, the method proceeds to 1010. Otherwise, the method proceeds to 1008.

At 1008, one or more band width metrics are determined. In one exemplary embodiment, the band width metric can include the thickness of the band, the circumferential extent of the band, the location of the band relative to other features of the component, or other suitable metrics. The method then proceeds to 1010.

At 1010, it is determined whether one or more other anomalies are present, such as by analyzing histogram data, binarizing image data, mapping image data, or other suitable processes. If it is determined that no other anomalies are present, the method proceeds to 1014. Otherwise, the method proceeds to 1012 where other metric data is determined, such as the size of an anomaly, the extent of a histogram data variation, or other suitable data. The method then proceeds to 1014.

At 1014, it is determined whether any metrics exceed predetermined allowable limits, such as whether the thickness or circumferential extent of a ring exceeds a predetermined allowable thickness or circumferential extent. If it is determined that no metric exceeds a limit, the method proceeds to 1016, where the component is accepted or the next feature is analyzed. Otherwise, the method proceeds to 1018 where the component is rejected or the next feature is analyzed. A feature database can likewise be updated to reflect the rejection of the feature, such as where a predetermined number of features can be rejected without rejecting the component.

In operation, method 1000 allows a component to be inspected using component illumination from two or more light sources, such as an axial light source and an off-axis light source. Method 1000 analyzes image data to locate one or more bands or other anomalies, and then compares the located bands or anomalies to one or more metrics (such as empirically or analytically determined metrics) to determine whether the bands or anomalies exceed the metric.

Although exemplary embodiments of a system and method of the present invention been described in detail herein, those skilled in the art will also recognize that various substitutions and modifications can be made to the systems and methods without departing from the scope and spirit of the appended claims.

The invention claimed is:

1. A system for inspecting components comprising:
   an axial lighting system illuminating the component with axial lighting to allow one or more features of the component to be located;
   an off-axis lighting system illuminating the component with off-axis lighting in the absence of the axial lighting to allow the component to be inspected to locate one or more features;
   an image analysis system receiving image data of the component and analyzing the image data utilizing gradient processing to compare a first gradient value to a second gradient value to locate the one or more features.

2. The system of claim 1, wherein the image analysis system analyzes a single set of the image data to locate the one or more features.

3. The system of claim 2 wherein the image analysis system further comprises a feature locator system receiving the image data and generating feature edge data.

4. The system of claim 2 wherein the image analysis system further comprises a defect locator system receiving the image data and generating defect indication data from the pixel data.

5. The system of claim 2 wherein the image analysis system further comprises a protrusion analysis system receiving the image data and generating projection size data.

6. The system of claim 2 wherein the image analysis system further comprises a recess analysis system receiving the image data and generating recess analysis data.

7. The system of claim 2 wherein the image analysis system further comprises a missing feature system receiving image data and generating missing feature data.

8. The system of claim 2 wherein the image data further comprises pixel data.

9. A system for inspecting components comprising:
an off-axis lighting system illuminating the component with off-axis lighting to allow the component to be inspected to locate one or more features corresponding to a plane of reference, one or more features extending above the plane of reference, and one or more features extending below the plane of reference; and
an image analysis system receiving image data of the component generated when the component is being illuminated with the off-axis lighting and analyzing at least three relative maxima of histogram data generated from the image data to locate the one or more features, respectively.

10. The system of claim 9 wherein the image analysis system further comprises a feature locator system receiving the image data and generating feature edge data.

11. The system of claim 9 wherein the image analysis system further comprises a defect locator system receiving the image data and generating defect indication data from the image data.

12. A method for inspecting a component comprising:
illuminating the component with off-angle lighting to increase the visibility of one or more types of features;
generating image data of the component; and
analyzing at least three relative maxima of histogram data generated with the image data to determine whether any of the one or more types of features are present.

13. The method of claim 12 wherein illuminating the component with the off-angle lighting comprises illuminating the component with a circular xenon flash lamp.

14. The method of claim 12 wherein generating the image data of the component comprises generating an N×M array of pixel data.

15. The method of claim 12 wherein analyzing the image data to determine whether any of the one or more types of features are present comprises analyzing the image data to determine whether a protrusion is present.

16. The method of claim 12 wherein analyzing the image data to determine whether any of the one or more types of features are present comprises analyzing the image data to determine whether a recess is present.

17. The method of claim 12 wherein analyzing the image data to determine whether any of the one or more types of features are present comprises analyzing the image data to determine whether a feature is missing.

18. The method of claim 12 wherein analyzing the image data to determine whether any of the one or more types of features are present comprises generating the histogram data from a single set of image data and determining whether the histogram data indicates that a feature is present.

19. The method of claim 12 wherein analyzing the image data to determine whether any of the one or more types of features are present comprises generating the histogram data from a single set of image data and determining whether the histogram data indicates that a recess is present.

20. The method of claim 12 wherein analyzing the image data to determine whether any of the one or more types of features are present comprises generating the histogram data from a single set of image data and determining whether the histogram data indicates that a protrusion is present.

21. A system for inspecting components comprising:
an axial lighting system illuminating the component with axial lighting to allow one or more features of the component to be located;
an off-axis lighting system illuminating the component with off-axis lighting to allow the component to be inspected to locate one or more features; and
a dual lighting analysis system analyzing image data of the component created when the axial lighting system and the off-axis lighting system are simultaneously illuminating the component and generating component acceptance data.

22. The system of claim 21 wherein the dual lighting analysis system further comprises a band analysis system receiving edge data and generating band data.

23. The system of claim 21 wherein the dual lighting analysis system further comprises an edge location system receiving pixel data and generating edge data.

24. The system of claim 21 wherein the dual lighting analysis system further comprises a feature analysis system receiving band data and determining whether a feature is present.

25. A system for inspecting components comprising:
an axial lighting system illuminating a component with axial lighting to allow one or more features of the component to be located;
an off-axis lighting system illuminating the component with off-axis lighting in the absence of the axial lighting to allow the component to be inspected to locate one or more features of the component; and
a band analysis system receiving image data of the component and analyzing the image data to identify two or more edges to determine whether a band between the two or more edges identifies the one or more features.

* * * * *

UNITED STATES PATENT AND TRADEMARK OFFICE
CERTIFICATE OF CORRECTION

| | | |
|---|---|---|
| PATENT NO. | : 7,024,031 B1 | Page 1 of 1 |
| APPLICATION NO. | : 10/035592 | |
| DATED | : April 4, 2006 | |
| INVENTOR(S) | : Ramiro N. Castellanos et al. | |

It is certified that error appears in the above-identified patent and that said Letters Patent is hereby corrected as shown below:

Title Page #56

Page 1, line 2 of "Other Publications", after "U.S." insert --parent--.

Drawings

Sheet 6 of 7 (Figure 8, Box 814, delete "MAXIMIM" and insert -- MAXIMUM --, therefore.

Column 2, lines 3-5, delete "The present invention provides for accurate estimates of the size of such protrusions and recesses to be made from a single set of image data" and insert the same on line 2, after "surfaces." as the continuation of the paragraph.

Column 7, line 47, before "65" insert --75--.

Signed and Sealed this

Tenth Day of April, 2007

JON W. DUDAS
*Director of the United States Patent and Trademark Office*